(12) United States Patent
Hunziker et al.

(10) Patent No.: US 6,730,513 B1
(45) Date of Patent: May 4, 2004

(54) KERATINOCYTE CULTURES AND USES THEREOF

(75) Inventors: Thomas Hunziker, Oberhofen (CH); Alain Limat, Tavel (CH)

(73) Assignee: Epitech SA, Tortola (VG)

( * ) Notice: Subject to any disclaimer, the term of this patent is extended or adjusted under 35 U.S.C. 154(b) by 0 days.

(21) Appl. No.: 09/546,269

(22) Filed: Apr. 10, 2000

Related U.S. Application Data

(63) Continuation-in-part of application No. 09/358,181, filed on Jul. 20, 1999, now Pat. No. 6,548,058.

(51) Int. Cl.$^7$ ................................................. C12N 5/00

(52) U.S. Cl. ....................................... 435/371; 424/93.7

(58) Field of Search ........................ 424/93.7; 435/371

(56) References Cited

U.S. PATENT DOCUMENTS

| | | |
|---|---|---|
| 5,580,781 A | 12/1996 | Naughton et al. ............ 435/1.1 |
| 5,968,546 A | 10/1999 | Baur |

FOREIGN PATENT DOCUMENTS

| | | |
|---|---|---|
| DE | 196 51 992 A1 | 6/1998 |
| WO | WO 93/08776 | 5/1993 |

OTHER PUBLICATIONS

International Search Report for International application No. PCT/IB00/01076.
Lenoir–Viale, M.C. et al., 1993, "Epidermis reconstructed from the outer root sheath of human hair follicle: Effect of retinoic acid." Archives of Dermatological Research, vol. 285, No. 4, pp. 197–204.
Limat, Alain et al., 1996, "Successful treatment of chronic leg ulcers with epidermal equivalents generated from cultured autologous outer root sheath cells." J. of Inv. Derm., vol. 107, No. 1, pp. 125–135.
*Brysk et al., 25 J. Am. Acad. Dermatol. 238–244(1991).
*Fabre, 29 Immunol. Lett. 161–166 (1991).
*Harris et al., 18 Clin. Exp. Dermatol. 417–420 (1993).
*Hetton et al., 14 J. Am. Acad. Dermatol. 399–405 (1986).
*Hunyadi et al., 14 J. Dermatol. Surg. Oncol. 75–78 (1988).
*Johnson et al., 11 J. Burn Care Rehab. 504–509 (1990).
*Leigh et al., 117 Brit. J. Dermatol. 591–597 (1987).
*Leigh et al., 11 Clin. Exp. Dermatol. 650–652 (1986).
*Mol et al., 24 J. Am. Acad. Dermatol. 77–82 (1991).
*Moll et al., 46 Hautarzt 548–552 (1995).
*Phillips et al., 21 J. Am. Acad. Dermatol. 191–199 (1989).
Eosem et al., Responses of the Superficial Portion of the Human Pilosebaceous Apparatus to Controlled Injury. *The Journal of Investigative Dermatology*, 15:145–155 (1955).
Montagna et al., The Structure and Function of Skin 172–258. (Academic Press New York, NY 1974).
Coulombe et al., Expression of Keratin K14 in the Epidermis and Hair Follicle: Insights into Complex Programs of Differentiation. *The Journal of Cell Biology*, 109:2295–2312 (1989).
Limat ea al., Restoration of the Epidermal Phenotype by Follicular Outer Root Sheath Cells in Recombinant Culture with Dermal Fibroblasts. *Experimental Cell Research*, 194:218–227 (1991).
Limat ea al., Outer root sheath (ORS) cells organize into epidermoid cyst–like spheroids when cultured inside Matrigel: a light–microscipie and immunohistological comparison between human ORS cells and interfollicular keratinocytes. *Cell & Tissue Research*, 275:169–176 (1994).
Cotsarelis et al., Label–Retaining Cells Reside in the Bulge Area of Pilosebaceous Unit: Implications for Follicular Stem Cells, Hair Cycle, and Skin Carcinogenesis. *Cell*, 61:1329–1337 (1990).
Kobayashi, et al., Segregation of keratinocyte colony–forming cells in the bulge of the rat vibrissa. *Proceedings of the National Academy of Sciences of the United States of America*, 90:7391–7395 (1993).
Yang et al., Upper Human Hair Follicle Contains a Subpopulation of Keratinocytes with Superior In Vitro Proliferative Potential. *The Journal of Investigative Dermatology*, 101(5):652–659 (1993).
Rochat, et al., Location of Stem Cells of Human Hair Follicles by Clonal Analysis. *Cell*, 76:1063–1073 (1994).
Moll et al., Proliferative Potential of Different Keratinocytes of Plucked Human Hair Follicles. *The Journal of Investigative Dermatology*, 105:14–21 (1995).
Weterings, et al., A method for culturing human hair follicle cells, *British Journal of Dermatology*, 104:1–5 (1981).
Limat and Noser. Serial Cultivation of Single Keratinocytes from the Outer Root Sheath of Human Scalp Hair Follicles. *The Journal of Investigative Dermatology*, 87:485–488 (1986).
Imcke, et al., Growth of human hair follicle keratinocytes in vitro. *Journal of the American Academy of Dermatology*, 17:779–786 (1983).
Limat et al., Post–Mitotic Human Dermal Fibroblasts Efficiently Support the Growth of Human Follicular Keratinocytes. *The Journal of Investigative Dermatology*, 92:758–762 (1989).

(List continued on next page.)

*Primary Examiner*—Jean C. Witz
(74) *Attorney, Agent, or Firm*—Mintz, Levin, Cohn, Ferris, Glovsky and Popeo, P.C.

(57) ABSTRACT

The present invention relates to the treatment of skin defects by organotypically-cultured autologous keratinocytes isolated from the outer root sheath of anagen or growing hair. Methods for primary, as well as subsequent organotypic cultures (i.e., epidermal equivalents) in fully-defined media supplemented by autologous human serum and substances isolated from blood components, with minimal allogeneic biological supplements, are disclosed herein. Techniques to prepare epidermal equivalents for transplantation by use of a biocompatible glue are also disclosed herein.

15 Claims, No Drawings

OTHER PUBLICATIONS

Stark, et al., Keratins of the human hair follicle: "Hyperproliferative" keratins consistently expressed in outer root sheath cells in vivo and in vitro. *Differentiation*, 35:236–248 (1987).

Limat et al., Experimental Modulation of the Differentiated Phenotype of Keratinocytes from Epidermis and Hair Follicle Outer Root Sheath and Matrix Cells. *Annals of The New York Academy of Sciences*, 642:125–147 (1991).

Lenoir et al., Outer Root Sheath Cells of Human Hair Follicle Are Able to Regenerate a Fully Differentiated Epidermis in Vitro, *Developmental Biology*, 130:610–620 (1988).

Limat et al., Formation of a Regular Neo–Epidermis by Cultrued Human Outer Root Sheath Cells Grafted on Nude Mice, *Transplantation*, 59:1032–1038 (1995).

O'Connor et al., Grafting of Burns With Cultured Epitehlium Prepared From Autologous Epidermal Cells. *The Lancet*, 1:75–78 (1981).

Compton, et al., Skin Regenerated from Cultured Epithelial Autografts on Full–Thickness Burn Wounds from 6 Days to 5 Years after Grafting. *Laboratory Investigation*, 60:600–612 (1989).

Carter et al., Treatment of junctional epidermolysis bullosa with epidermal autografts. *Journal of the American Academy of Dermatology*, 17:246–250 (1987).

Dean et al., The Use of Cultured Epithelial Autograft in a Patient with Idiopathic Pyoderma Gangrenosum. *Annals of Plastic Surgery*, 26:194–195 (1991).

Limova and Mauro. Treatment of Pyoderma Gangrenosum with Cultured Keratinocyte Autografts. *The Journal of Dermatologic Surgery and Oncology*, 20:833–836 (1994).

Gallico et al., Cultured Epithelial Autografts for Giant Congenital Nevi, *Plastic and Reconstructive Surgery*, 84:1–9 (1989).

Higgins et al., use of two stage keratinocyte–dermal grafting to treat the separation site in conjoined twins. *Journal of the Royal Society of Medicine*, 87:108–109 (1994).

KERATINOCYTE CULTURES AND USES THEREOF

This is a CIP of Ser. No. 09/358,181, filed Jul. 20, 1999, now U.S. Pat. No. 6,548,058.

FIELD OF THE INVENTION

The invention relates to the field of cell culture of human keratinocyte precursor and dermal fibroblast cells. The invention also relates to the use of cultured keratinocyte precursor cells in the repair of skin defects by skin grafting procedures.

BACKGROUND OF THE INVENTION

The healing of skin defects progresses through three general phases: (i) inflammation, (ii) wound cell migration and mitosis, and (iii) extracellular matrix production and remodeling. The ordered sequence of these events is thought to be orchestrated by interactions among cells, growth factors, and extracellular matrix proteins. A crucial step of skin wound healing is epidermal regeneration (i.e., re-epithelialization). Besides interfollicular epidermal keratinocytes from the wound edges, the outer root sheath (ORS) cells from residual hair follicles also contribute to this process (see e.g., Eisen et al., 15 J. Invest. Dermatol. 145–155 (1955)). The ORS of hair follicles is comprised largely of undifferentiated keratinocytes that encompass the cylindrical structures of the hardened inner root sheath and the hair shaft (see e.g., Montagna & Parakkal, In: *The Structure and Function of Skin* 172–258 (Academic Press New York, N.Y., 1974)). Recent literature has also indicated that ORS cells are at a lower level of commitment to differentiation than the basal interfollicular keratinocytes (see e.g., Coulombe et al., 109 J. Cell Biol. 2295–2312 (1989); Limat et al., 194 Exp. Cell Res. 218–227 (1991); Limat et al., 275 Cell Tissue Res. 169–176 (1994)), and label-retaining cells have been detected in the animal as well as the human ORS region near the bulge area which possibly represent stem cells for skin epithelial tissues (see e.g., Cotsarelis et al., 61 Cell 1329–1337 (1990); Kobayashi et al., 90 Proc. Nat. Acad. Sci. USA 7391–7395 (1993); Yang et al., 105 J. Invest. Dermatol. 14–21 (1993); Rochat et al. 76 Cell 1073–1076 (1994); Moll, 105 J. Invest. Dermatol. 14–21 (1995)). Additionally, human ORS cells which are isolated from plucked anagen scalp hair follicles can be expanded extensively in vitro (see e.g., Weterings et al., 104 Brit. J. Dermatol. 1–5 (1981); Limat & Noser, 87 J. Invest. Dermatol. 485–488 (1986); Imcke et al., 17 J. Am. Acad. Dermatol. 779–786 (1987); Limat et al., 92 J. Invest. Dermatol. 758–762 (1989)). Under conventional submerged culture conditions, ORS cells resemble interfollicular epidermal keratinocytes by both morphologic and biochemical (e.g., keratin profiles) criteria (see e.g., Stark et al., 35 Differentiation 236–248 (1987); Limat et al., 92 J. Invest. Dermatol. 758–762 (1989); Limat et al., 642 Ann. N.Y. Acad. Sci. 125–147 (1991)). In organotypic co-cultures with human dermal fibroblasts (i.e., under conditions mimicking the epidermal environment), ORS cells with respect to histological, immunohistological, ultrastructural and biochemical criteria develop a stratified epithelium reminiscent of regenerating epidermis (see e.g., Lenoir et al., 130 Dev. Biol. 610–620 (1988); Limat et al., 194 Exp. Cell Res. 218–227 (1991); Limat et al., 642 Ann. N.Y. Acad. Sci. 125–147 (1991)). If such organotypic cultures are grafted onto nude mice, ORS cells form a regular neo-epidermis that is under homeostatic control (see e.g., Limat et al., 59 Transplantation 1032–1038 (1995)). Thus, human ORS cells are of considerable interest for clinical application.

In the previous decade, interest has focused on the use of cultured epithelial cells for wound coverage. First, sheets of cultured autologous interfollicular keratinocytes were grafted successfully on acute wounds, mainly in the treatment of larger third degree burns (see e.g., O'Connor et a., 1 Lancet 75–78 (1981); Compton et al., 60 Lab. Invest. 600–612 (1989)) but also of epidermolysis bullosa (see e.g., Carter et al., 17 J. Am. Acad. Dermatol. 246–250 (1987)), pyoderma gangrenosum (see e.g., Dean et al., 26 Ann. Plast. Surg. 194–195 (1991); Limova & Mauro, 20 J. Dermatol. Surg. Oncol. 833–836 (1994)), and wounds after excision of giant congenital nevi (see e.g., Gallico et al., 84 J. Plast. Reconstr. Surg. 1–9 (1989)) or separation of conjoined twins (see e.g., Higgins et al., 87 J. Royal Soc. Med. 108–109 (1994)).

In contrast to the treatment of such acute wounds, the grafting of chronic wounds (e.g., leg ulcers) with cultured keratinocytes has been much less successful. Allografts do not result in a permanent "take" (see e.g., Fabre, 29 Immunol. Lett. 161–166 (1991)) and thus may be classified as a "quite effective but expensive biological dressing" (see Phillips et al., 21 J. Am. Acad. Dermatol. 191–199 (1989). A reproducible, major definite "take" of autologous keratinocyte grafted by various modalities including: sheets of submerged keratinocyte cultures consisting of only a few, noncornified cell layers (Hetton et al., 14 J. Am. Acad. Dermatol. 399–405 (1986); Leigh & Purkis, 11 Clin. Exp. Dermatol. 650–652 (1986); Leigh et al, 117 Brit. J. Dermatol. 591–597 (1987); Harris et al., 18 Clin. Exp. Dermatol. 417–420 (1993)), trypsinized single cells attached to collagen-coated dressings (Brysk et al., 25 J. Am. Acad. Dermatol. 238–244 (1991)), skin equivalents (Mol et al., 24 J. Am. Acad. Dermatol. 77–82 (1991)) has yet to be convincingly documented within the scientific literature. The same lack of quantitative findings also holds true for various reports on the grafting of freshly isolated, autologous interfollicular keratinocytes (Hunyadi et al., 14 J. Dermatol. Surg. Oncol. 75–78 (1988)) or ORS cells (Moll et al., 46 Hautarzt 548–552 (1995)) fixed to the wound bed by the use of a fibrin glue. However, it should be noted that the disadvantages of the bovine serum used during cultivation of the keratinocytes may contribute to reduced "take" rate, due to the fact that it resists in keratinocytes (see e.g., Johnson et al, 11 J. Burn Care Rehab. 504–509 (1990)).

SUMMARY OF THE INVENTION

Prior to the disclosure of the present invention herein, the standard methodology for the generation of a primary culture of ORS keratinocytes consisted of the plucking of an anagen (i.e., growing hair shaft) hair followed by a careful microscopic dissection to remove the hair bulbs and the infundibular hair shaft. The resulting outer root sheath was then placed on the culture insert for initiation of the primary keratinocyte culture. However, numerous subsequent studies (approximately 200), wherein the anagen hair was placed directly on the culture insert without performing the initial micro-dissection to remove the hair bulbs and the infundibular hair shaft, have demonstrated that such tedious and time-consuming dissection of the plucked anagen hair was not required. This has served to markedly simplify the handling process, reduce the risk for contamination, and resulted in more efficient initiation of keratinocyte cell plating.

Accordingly, it is an object of the present invention to provide improved and simplified methods for the generation of keratinocytes or keratinocyte precursors from outer root sheath cells (ORS cells) in fully defined culture conditions for the treatment of various types of skin defects (e.g., chronic wounds such as leg ulcers, diabetic ulcers, pressure sores, and the like) in both humans and animals. In addition to their use in the treatment of wounds, keratinocytes may also be used in plastic and cosmetic surgery, or whenever there is a demand for such skin support (e.g., post operative following the removal of tattoos, naevi, skin cancer, papillomas, after amputation, in sex transformation or re-virgination, rejuvenation of actinically damaged skin after skin resurfacing, tympanoplasty, epithelialization of external ear canal, and the like).

These aforementioned objectives are accomplished by explantation and culture of plucked, anagen or growing hairs in toto upon microporous membranes carrying human fibroblast feeder cells at their under-surface. In such primary cultures, large numbers of ORS cells can be easily and repeatedly obtained, irrespective of the donor's chronological age. Such ORS cells may be used for the subsequent preparation of complex skin, i.e., dermo-epidermal, or epidermal equivalents or kept frozen and stored in order to use them at a later time point.

The subsequent preparation of skin or epidermal equivalents is achieved by the "seeding" of these ORS cells upon a modified, microporous membrane carrying fibroblast feeder cells (most preferably growth-arrested/limited human dermal fibroblast "feeder cells") at their under-surface. During culture, these ORS cells undergo tissue differentiation which has been demonstrated to be similar to that of normal epidermis. This finding is most probably due to a large compartment of proliferating cells. The modified culture conditions which are disclosed herein are important for the successfull treatment of chronic wounds with epidermal equivalents generated in vitro from autologous ORS cells.

A further object of the present invention is to provide improved culture systems for ORS-derived keratinocytes by adhering the anagenic hair onto a polymeric microporous membrane coated with one or more molecules of extracellular matrix origin. These improved cultures of ORS cells, designated as skin equivalents or epidermal equivalents, may be used to treat skin defects, especially chronic wounds.

Yet another object of the present invention is to produce skin or epidermal equivalents using a reduced concentration of allogenic or homologous serum. This greatly mitigates the risk of disease transmission, for example, by clinical use of blood products, by the use of autologous or homologous human serum and substances derived or released from blood components (e.g., blood platelets) for supplements in in vitro culturing steps.

A further object of the present invention is a methodology which reduces the probability of mechanical damage (e.g., separation of the various constituent layers) of the skin or epidermal equivalents during transport prior to transplantation.

The clinical advantages of the methodology of the present invention, as compared to grafting techniques of chronic wounds which have been previously utilized, include, but are not limited to: noninvasiveness (so that the cells are available repeatedly), the lack of need for surgical facilities or anesthesia during the grafting procedure, and a short immobilization period of only 2 hours required following the grafting procedure.

DETAILED DESCRIPTION OF THE INVENTION

Unless defined otherwise, all technical and scientific terms used herein have the same meanings commonly understood by one of ordinary skill in the art to which this invention belongs. Although any methods and materials similar or equivalent to those described herein can be used in the practice of the present invention, the preferred methods and materials are now described. All publications mentioned herein are incorporated herein in their entirety by reference.

The term "keratinocyte layer" as used herein means an in vitro generated keratinocyte tissue culture with more or less differentiated structure. The term "epidermal equivalent" as used herein means an in vitro generated organotypic tissue culture resembling in its histological structure the natural epidermis especially concerning the stratification and development of the horny layer. A normal stratified epidermis consists of a basal layer of small cuboidal cells, several spinous layers of progressively flattened cells, a prominent granular layer and an orthokeratotic horny layer. All these layers can be detected in the epidermal equivalents that are subject of the invention. Localization of those epidermal differentiation products that have been assayed by immunohistochemistry (e.g. keratins, involucrin, filaggrin, integrins) is similar to that found in normal epidermis.

The term "autologous" as used herein means: (i) that biological material to be transplanted is derived from the individual to be treated with epidermal equivalents; or (ii) that biological material added to tissue cultures comes from the donor of the cells for tissue culture.

The term "homologous" as used herein means: (i) that biological material to be transplanted is derived from one or more individuals of the same species as the individual to be treated with epidermal equivalents; or (ii) that biological material added to tissue cultures comes from one or more individuals of the same species as the donor of cells for the tissue culture.

The term "organotypic culture" and the like, refers to culture of cells under conditions that promote differentiation of the cells. Under conditions of organotypic culture, proliferation of the cells is slowed compared to culture under "proliferative" conditions such as primary culture conditions, and may be completely stopped. In the present case, an important condition for organotypic culture is maintenance of the cells at the air-liquid interface, a so-called "lifted" culturing condition.

The term "relcasate from blood components" (e.g., blood platelets) as used herein means any combination of cytokines or other growth factors obtained from blood components (e.g., blood platelets). Platelets stimulated with, for example, thrombin release the content of their alpha granules into the surrounding medium. Alpha granules usually contain several cytokines (e.g., platelet derived growth factor (PDGF), epidermal growth factor (EGF), transforming growth factors alpha and beta (TGF alpha/beta), platelet factor 4 (PF-4), platelet basic protein (PBP)). However, it is possible to obtain cytokines and other growth factors from platelets by other methods than stimulating with thrombin. Moreover, other blood components produce growth factors and cytokines as well. Monocytes, for example, produce IL-1, TNF alpha, IL-6 and other substances of interest.

General Method for Preparing Epidermal Equivalents from ORS Cells

Keratinocyte precursor cells are selected from outer root sheath (ORS) of anagen or growing hair which is derived from the individual which is to be subsequently treated with epidermal equivalents. In general, approximately 40 hair follicles are plucked from the scalp, and those in the anagen phase (i.e., a growing hair shaft) are then selected under the dissecting microscope. A total of four weeks of culture is usually required in order to obtain approximately 1 cm$^2$ of epidermal equivalents from five hair follicles. However, with improved culture and fermentation techniques it may be possible to get a higher yield (i.e., a larger area of epidermal equivalents, within this period of time).

The previous standard method for the generation of a primary culture of ORS keratinocytes consisted of the plucking of an anagen (ie., growing hair shaft) hair followed by a careful microscopic dissection to remove the hair bulbs and the infundibular hair shaft. The resulting outer root sheath (ORS) was then placed on the culture insert for initiation of the primary keratinocyte culture. However, numerous subsequent studies (approximately 200), wherein the anagen hair was placed directly on the culture insert without performing the initial micro-dissection to remove the hair bulbs and the infundibular hair shaft, have demonstrated that such tedious and time-consuming dissection of the plucked anagen hair was not required. This has served to markedly simplify the handling process, reduce the risk for contamination, and resulted in more efficient initiation of keratinocyte cell plating.

The selected anagen hairs were incubated in an appropriate rinsing buffer containing various anti-microbial and anti-fungal agents (e.g., fungizone, penicillin, and streptomycin). Following this procedure, the entire plucked anagen hair is placed directly on the culture insert and allowed to grow for several days, preferably 7–14, days, and more preferably 8 to 10 days. An optional, additional step is comprised of passaging the primary culture and performing a secondary culture in order to obtain more cellular material for the preparation of larger areas of epidermal equivalents.

The culture insert, a microporous membrane coated with one or more extracellular matrix substances (e g., fibrin, fibronectin, collagens, laminins or hyaluronan or mixtures thereof), carries a growth-arrested/limited feeder cell system on its undersurface. The coating of the membrane insert with such extracellular matrix substances provides for: (i) an enhanced culture surface for the initial attachment of the anagen hair (i.e., it sticks easily and remains stationary); (ii) a surface which significantly enhances the migration of the ORS keratinocytes away from the outer root sheath (ORS) anagen hair follicles; and (iii) increased growth rates of the spreading ORS keratinocytes (ie., the overall culture time needed for production of fully differentiated skin or epidermal equivalents) can be reduced to three weeks, instead of four.

The aforementioned growth-arrested/limited feeder cell system located on the under surface of the microporous insert membrane is comprised of primary dermal fibroblasts obtained from a human skin biopsy. The primary dermal fibroblasts are treated with mitomycin-C for 4 to 6 hours prior to their use as a "feeder cell layer" for the plucked anagen hair and then plated on the underside of the culture insert. Growth arrest/limitation is induced by either mitomycin-C or X-ray treatment or, preferably, the reduced serum concentration below 5%, and preferably 2%. It should be noted that, although some cultures had been performed using 10% fetal calf serum (FCS; Boehringer Mannheim, Germany), the current utilization of human serum, in order to reduce the number of allogeneic ingredients, was found to provide markedly superior outgrowth and proliferation of the ORS cells. Moreover, the human serum is preferably utilized in a concentration of less than 5%, and more preferably in a concentration of 2%. In the presence of such low serum concentrations, the primary human dermal fibroblasts of the present invention will become significantly, or completely growth arrested. Hence, in this manner, two expensive and potentially complicating steps in the autologous ORS culture system may be removed. The two complicating steps include: (i) removal of high serum >5% concentrations, which reduces the overall cost of the process significantly and; (ii) the removal of mitomycin-C treatment, which provides a fully mitomycin-C-free culture system and eliminates any concerns regarding the total elimination of the drug from the primary culture inserts prior to the growth of the epidermal equivalents. In addition, the use of reduced serum concentrations allows the alternative feeder cell-arresting procedure (i.e., the X-ray exposure step) to be eliminated, thus saving significant time and expense in the overall procedure.

Following expansion of the ORS cells to an appropriate density (i.e., $1 \times 10^3$ to $1 \times 10^6$ cells/cm$^2$, and preferably $5 \times 10^4$ to $1 \times 10^5$ cells/cm$^2$), they are used for preparation of epidermal equivalents. Preferably, the cells are grown to confluence. The epidermal equivalents are prepared by seeding ORS cells at an appropriate cell density (i.e., $30 \times 10^3$ to $100 \times 10^3$ cells/cm$^2$, and preferably $60 \times 10^3$ cells/cm$^2$) within a culture device which is suitable for "lifting" the cells up to the air-liquid interface during culture. Subsequently, one to four days after seeding (preferably 3 days after seeding), the ORS cells are exposed to air (e.g., by aspiration of the medium inside the insert) and the cultures are then continued for approximately 10–20 days, and preferably for 14–18 days, in such "lifted" culture condition. The medium is changed periodically during the lifted culture; preferably every two to three days.

The present invention also encompasses skin equivalents which include additional layers, and so are more complex structures than epidermal equivalents. Skin equivalents comprise differentiated ORS cells as their epidermal part and also a layer comprising a matrix component, preferably one containing embedded dermal fibroblasts and/or other cells (ie., an "embedding matrix"). Skin equivalents are made by placing a matrix with one or more extracellular matrix substances (e.g., fibrin, fibronectin, collagens, laminins or hyaluronan or mixtures thereof) on the upper surface of the microporous membrane described above. When embedding human dermal fibroblasts, preferably autologous human dermal fibroblasts, the cells are embedded at a density of $1 \times 10^3$ to $1 \times 10^7$ cells/cm$^3$; preferably $1 \times 10^4$ to $1 \times 10^5$ cells/cm$^3$; and most preferably approximately $5 \times 10^4$ cells/cm$^3$. The primary culture of ORS cells is then seeded on top of the matrix (preferably containing embedded dermal fibroblasts and/or other cells) and organotypic culturing is performed as described above. For a detailed description of the preparation of dermal equivalents (see e.g., Limat et al., 194 Exp. Cell Res. 218–277 (1991)).

It should be noted, however, that the cells which are embedded in the matrix need not be limited exclusively to dermal fibroblasts; as epidermal, mesenchymal, neuronal and/or endothelial cells can also be utilized. The embedded cells are preferably obtained from skin tissue, are more preferably allogeneic cells, and are most preferably autologous cells.

All culture steps are performed in an appropriate medium which allows the proliferation of the ORS cells and their outgrowth from the hair follicles, the medium is typically changed every 2 to 3 days. Generally, the medium utilized for all steps is the same. The medium is typically based on a minimal medium and contains several additional ingredients. One common ingredient is serum in a concentration of 0.5–60%. In the preferred embodiment of the present invention, human serum is used at a concentration of less than 5%, and most preferably at a concentration of 2%. Furthermore, with the development of serum-free media, it may be possible to omit serum in toto. Epidermal growth factor (EGF) stimulates migration of keratinocytes and delays their senescence which results in stimulation of proliferation. Cholera toxin, hydrocortisone, insulin, adenine and triiodothyronine have an effect of stimulating proliferation. All of these ingredients are thus useful in a medium for preparing epidermal equivalents. Nevertheless, it may be possible to omit or replace one or another of these ingredients.

Releasate from blood components (e.g., blood platelets, monocytes or lymphocytes), may serve as a source of cell proliferating activities, and therefore may substitute serum and provide other above mentioned ingredients. For certain culture periods the serum-containing medium might possibly be replaced by a defined, serum-free medium, for example, SFM (Gibco Europe ettlingen). The releasate from blood components (e.g., blood platelets, monocytes or lymphocytes), especially of homologous or autologous origin, may serve as a source of cell proliferating activities and therefore may substitute serum and provide other above mentioned ingredients or indeed may provide additional ingredients. The blood components should be added to the culture medium in a concentration of 0.1% to 20%, and preferably 1% to 5%, after the releasate is brought-to the same final volume as the blood from which these components are obtained. These releasates contain several growth factors that are present in serum (e.g., PDGF, ECF or TGFs). However, serum as well as releasates contain many substances, and not all are characterized.

Releasate from blood platelets is obtained by centrifugation of anti-coagulated whole blood, preferably human blood, in order to pellet all cells except thrombocytes. The supernatant is centrifuged once more to spin down the thrombocytes. The thrombocytes are suspended in an appropriate buffer, e.g. phosphate buffer and treated with thrombin in order to release their alpha granules which contain a mixture of various growth factors (e.g., PDGF, PF-4, TGF-β, EGE, β-thromboglobulin). In a further centrifugation step all cellular material is removed. Finally, the supernatant is supplemented with buffer to the volume of the original blood sample from which the components are obtained. The blood components should be added to the culture medium in a concentration of 0.1% to 20%; preferably 1% to 10%; and more preferably 2 to 5%.

Similarly, releasates can be obtained from other blood cells, such as monocytes, by breaking up the cells (e.g., by sonication, freeze-thaw method, or the like) and purifying the growth factors (e.g., by filtration or immunological methods).

The blood component releasates can also be used to condition the wound bed in the course of grafting the epidermal or dermal equivalents. Furthermore, the culture medium containing the releasates and used to perform the organotypic culturing step, after having been conditioned by the cells, can be used to condition the bed of the skin defect in the course of grafting the epidermal or dermal equivalents.

Cultivation usually is performed in inserts with microporous membranes, which contain homologous or autologous human dermal fibroblasts (HDF), especially postmitotic HDF at their undersurface. HDF secrete factors that condition the medium in order to get a better growth of the epidermal equivalents. The HDF layer can be formed from between $5 \times 10^3$ to $1 \times 10^5$ cells/cm$^2$, and preferably approximately $1 \times 10^4$ to $5 \times 10^4$ cells/cm$^2$. The HDF are preferably postmitotic, but earlier passage cells can be used if they are irradiated, treated with mitomycin-C, or otherwise treated to inhibit their proliferation but maintain their metabolism, i.e., by reduction of serum concentration.

Microporous membranes are suitable as a culture substrate, because they allow substances to diffuse from one side to the other, but work as a barrier for cells. The pore size of the membrane is not a limitation on the present invention, but should be adequate so as to allow diffusion of proteins of up to 100,000 Daltons molecular weight, and preferably of up to 70,000 Daltons molecular weight. The membrane should at least allow diffusion of small hormones such as insulin, and allow passage of proteins of up to 15,000 Daltons molecular weight. Other means than a microporous membrane for performing the function of allowing diffusion of soluble factors to the cultured ORS cells, while preventing mixing of the ORS cells with the HDF would also be usable.

The microporous membranes typical in the art are usually used. However, membranes fabricated from a biodegradable material (e.g., polyhyaluronic acid or polylactic acid) can also be used. When a biodegradable microporous membrane is employed it is contemplated that the entire culture, including the differentiated ORS cells, the microporous membrane and the HDF, will be transplanted into the skin defect. Thus, in this alternative embodiment, the HDF grown on the underside of the membrane need not be post-mitotic or treated to preclude proliferation. While HDF tend to be less immunogenic than keratinocytes, it is preferable that when this embodiment is employed, the HDF be allogeneic cells, preferably autologous cells.

The epidermal equivalents of the present invention may range in size from approximately 6 mm to approximately 2.5 cm in diameter, with a preferred diameter of 2.5 cm. For practical reasons, the experiments disclosed herein were performed with epidermal equivalents of approximately 2.5 cm in diameter. Further clinical treatments will be performed so as to ascertain whether this size is generally applicable, or if other sizes will be more convenient for use in some cases.

In many cases, however, the skin or epidermal equivalents will have to he delivered from the facility where they are generated to the institution where they are used. Therefore a system is needed to enable the transport of the skin or epidermal equivalents, which have been kept in a condition ready for grafting. Irrespective of whether the microporous membrane is removed from the basal cell layer before transport, conditions resembling those during cultivation seem to be favorable. In order to keep the skin or epidermal equivalents in contact with medium only from the basal layer, (i.e., during cultivation), agarose in a concentration ranging from 0.1% to 5%, and preferably in a concentration of 0.5% to 1%, or methyl cellulose, or any other gelifying substance in comparable concentrations, may be used to solidify the transport medium. The skin or epidermal equivalents will be placed with their basal layer down on the membrane of an insert previously embedded on top of the solidified or gelled medium. The multiwell dish containing these inserts is then put in a blister sealed by a tyvek cover, and shipped. The skin or epidermal equivalents are, most preferably, used for grafting within 24 to 48 hours of initial packaging.

To improve the stability of the epidermal equivalents, the technique of placing a carrier membrane on top, ie., onto the cornified aspect, of the epidermal equivalents and eventually adhering to it was developed. As an adhesive, fibrin glue is preferred, however, other options, including, but not limited to: extracellular matrix components such as collagen, fibronectin, proteoglycans (e.g., hyaluronic acid, chondroitin sulfate, and the like), or basement membrane zone components (e.g., laminin, Matrigel™, or L-polylysine), or similar tissue glues, may also be utilized.

The carriers utilized in the present invention may consist of a synthetic membrane, made from at one or more of the following materials (polyester, PTFE or polyurethane); from one or more biodegradable polymers (e.g., hyaluronic acid, polylactic acid or collagen); or a silicone or vaseline gauze dressing, or any other material suitable for wound dressing. These materials which are suitable for wound dressing allow the carrier to remain in place to immobilize the implanted dermal or epidermal equivalents for several days, rather than requiring the carrier to be removed immediately after the dermal or epidermal equivalents are transplanted. Thus, the carrier not only enhances stability and improves handling, but it also serves as a protective coat against physical damage as well as the proteolytic milieu and bacteria in the wound. Moreover, it serves for orientation of the graft (i.e., basal side down, cornified side up).

The skin or epidermal equivalents put onto the carrier have to be kept in a condition ready for grafting. Irrespective of whether the microporous membrane is removed from the basal cell layer for transport, conditions resembling those during cultivation seem to be favorable. In order to keep the skin or epidermal equivalents in contact with medium only from the basal layer (i.e., during cultivation), agarose in a concentration ranging from 1% to 5%, and preferably in a concentration of 1 to 3%; methyl cellulose; or any other gelifying substance in comparable concentrations, may be used to solidify the medium. The epidermal equivalents together with the carrier will be placed with their basal layer on top of the solidified or gelled medium. The whole device is then sealed in an air tight manner, and shipped. The epidermal equivalents are, most preferably, used for grafting within 24 hours of initial packaging.

The skin or epidermal equivalents are transplanted by simply placing them in the bed of the wound or other skin defect. Preferably the skin or epidermal equivalents are then immobilized (patients are immobilized for 2 hours). The preferred method for immobilization is by use of a biodegradable material, by some sort of tissue glue or adequate bandage. As previously described, the bed of the skin defect can be treated with blood releasates or the medium from the organotypic culturing prior to, or concomitantly with, the transplantation.

EXAMPLE 1

Preparation of OHS Cells

Keratinocyte precursor cells from the outer root sheath (ORS) of the hair follicles are selected and subsequently cultured by use of the following methodology, as disclosed in the present invention.

Approximately 40 hair follicles were plucked with tweezers from the occipital scalp of individuals, and those in the anagen phase, as detected, for example, by well-developed root sheaths, were then selected under the dissecting microscope (see e.g., Limat & Noser, 87 J. Invest. Dermatol. 485–488 (1986); Limat et al., 92 J. Invest. Dermatol. 758–762 (1989)). The anagen hair was placed directly on the microporous culture insert without performing the previously-utilized micro-dissection to remove the hair bulbs and the infundibular hair shaft.

Generally, six anagenic hairs were explanted on the microporous membrane of a cell culture insert (Costar) that carried on its undersurface a preformed feeder layer preferably comprised of $20 \times 10^3$ postmitotic human dermal fibroblasts (HDF) per $cm^2$. (see e.g., Limat et al., 92 J. Invest. Dermatol. 758–762 (1989)). The HDFs were derived from skin explants of a healthy, repeatedly HIV-serology negative and hepatitis-serology negative individuals and cultured in DMEM supplemented with 10% fetal calf serum (FCS), or preferably less than 5% human serum, or most preferably 2% human serum.

For the purpose of obtaining an efficient outgrowth of the outer root sheath (ORS) cells from the anagen hair and a high proliferation rate, it is important not to place the HDF feeder cells at the bottom of the culture dish, resulting in an additional medium layer between the HDF layer and the microporous membrane supporting the ORS cells. Growing each cell type at one side of the microporous membrane allows a very close interaction, but prevents cross contamination of the ORS cells with fibroblasts and thus guarantees a pure culture of ORS cells.

The culture medium which was utilized consisted of Dulbecco's modified Eagle's medium/F12 (3:1 v/v) supplemented with 2% human serum, 10 ng of epidermal growth factor per ml of culture medium, 0.4 microgram of hydrocortisone per ml, 0.135 mM adenine, and 2 nM triiodothyronine (all obtained from Sigma Chemical Co., St. Louis, Mo.). The preferred final $Ca^{2+}$ concentration of the culture medium is 1.5 mM (see e.g, Wu et al., 31 Cell 693–703 (1982); Limat & Noser, 87 J. Invest Dermatol. 485–488 (1986)). Within about 2 weeks, the ORS cells had expanded and reached confluence. They were dissociated with 0.1% trypsin/0.02% EDTA mixture, checked for viability, and used for preparation of epidermal equivalents. It should be noted that, although initial cultures had been performed using 10% fetal calf serum (FCS; Boehringer Mannheim, Germany), current utilization of human serum, in order to reduce the number of allogeneic ingredients, provided superior outgrowth and proliferation of the ORS cells. The human serum is preferably utilized in a concentration of less than 5%, and most preferably in a concentration of 2%.

Explanting plucked anagen hairs directly on the membrane of culture inserts carrying postmitotic HDF on the undersurface as feeder cells proved to be a simple, efficient, and reproducible method for establishing primary cultures of ORS cells. Approximately 80% of the explanted hair follicles gave rise to outgrowth of ORS cells, even when derived from individuals aged more than 90 years. After 14 days, large areas of the insert were covered by compactly arranged small cells, at which time they were used for preparation of epidermal equivalents of the present invention.

The comparison of the growth behavior of 70 strains of ORS cells, which were derived from a total of 30 donors, demonstrated no significant differences between the young (i.e., 21 donors aged 19–50 years) and the old (ie., 9 donors aged 51–93 years) donors. Approximately $5 \times 10^5$ cells were generally obtained per explanted follicle and the overall degree of cell viability was typically higher than 95%. In contrast, in the absence of postmitotic HDF as a feeder layer, there was only sporadic outgrowth of ORS cells from the explanted follicles.

EXAMPLE 2

Preparation of Epidermal Equivalents

ORS cells harvested from primary cultures were seeded at a density of $30 \times 10^3$ cells/$cm^2$ to $100 \times 10^3$ cells/$cm^2$, and preferably 60×10³ cells/cm², on cell culture inserts (Costar) which had been previously inoculated with 10×10³ cells/cm² to 50×10³ cells/cm², and preferably 20×10³ cells/cm², of postmitotic HDF cells on the undersurface of their microporous membrane. Similar to the culture of ORS cells, it is important to keep the HDF feeder cells in close proximity with the ORS cells, while concomitantly keeping them separated by use of the microporous membrane. This culture technique enhances proliferation, differentiation, and thus the homeostasis of the developing tissue.

Culture medium was identical that that utilized for the preparation of the primary cultures as described supra. After 72 hours, the ORS cells were exposed to air by aspiration of the liquid medium inside the insert (i.e., leaving the underside of the insert in contact with medium) and cultured for an additional 12–14 days, with three medium changes per week. Alternatively, after one week lifted culture serum may be totally omitted.

For transplantation, the so-far-utilized protocol, which is generally employed for preparation of the fully differentiated epidermal equivalent for wound grafting, requires the physician to carefully cut the entire perimeter of the culture insert with a scalpel blade so as to facilitate the release of the insert membrane (with undercoated human dermal fibroblasts) with the attached skin patch squamous-side up. The skin patch is then released from this membrane by peeling with a fine forceps and placed, basal-side up, on a new membrane disk in a culture dish for eventual transplant to the patient. This aforementioned procedure is both laborious and time consuming, and can lead to reversal of the basal and squamous orientation.

A markedly simpler method which utilizes a carrier membrane patch cap has been devised which utilizes a membrane patch cap (analogous to the fibrin glue patch procedure described below) which is placed directly on top of the squamous surface layer. The membrane cap can then be easily grasped together with the skin patch below using fine forceps and peeled from the culture insert well surface, and, e.g., after incubation in diluted Dispase solution, be peeled from the culture insert membrane. The membrane can then serve a plate for placing the graft onto the wound without mixing up the orientation of the graft (i.e., basal side down, squamous side up).

For stabilization and as a protective coating in case of grafting, the epidermal equivalents of the present invention are coated on top with diluted fibrin glue, which also serves to clearly identify the upper (i.e., cornified) side. Fibrin glue, the preferred embodiment of the present invention, is a generally accepted, natural human product which is used extensively as a tissue glue. By applying a thin coating of fibrin glue (which is clearly visible with the naked eye) to the cornified squamous air-exposed surface of the epidermal equivalent, the physician placing the epidermal equivalent onto the wound site will be fully assured of proper graft orientation (ie., the basal surface of the skin patch will always be the side that does not have the clearly visible fibrin glue cap). Previously, in many instances, during the preparation of the epidermal patch for wound grafting, the orientation of the patch becomes confused. Should the skin patch be placed in squamous-side down orientation onto the graft site, there would be significantly decreased likelihood of a successful graft. Thus, the use of this simple "marking" completely eliminates this problem.

In addition, anti-microbial and/or anti-fungal substances may also be included in the fibrin glue, so as to impede any possible microbial contamination or overgrowth of the graft. Many chronic lesions are chronically-infected, which can result in the inhibition of graft "take" and subsequent wound healing following the initial skin grafting. Moreover, the addition of one or more antibiotics or anti-fungal agents by direct emulsification within the fibrin glue surface cap, may provide a significant improvement in the delivery of sufficient quantities of anti-microbial agents to the transplant site.

It should be noted that the ORS cells which were harvested from primary cultures, and cultured at the air-liquid interface on insert membranes carrying postmitotic HDF at their undersurface, typically developed a stratified epithelium within 14 days. This stratified epithelium consisted of a basal layer of small cuboidal cells below a thick suprabasal compartment of progressively flattened cells. A prominent granular layer, as well as an orthokeratotic horny layer were also found to be present.

Based upon the experimental finding of approximately 80% of the follicles giving rise to ORS cell outgrowth, approximately five anagen hair follicles were required for the generation of 1 cm² of epidermal equivalents. The period to generate graftable epidermal equivalents usually was four weeks in toto (i.e., two weeks for the primary culture and two weeks for the subsequent organotypic culture).

EXAMPLE 3

Stabilization

Before delivery, the epidermal equivalents are "coated on-top" by placing a silicone membrane of an appropriate diameter onto the cornified upper aspect of the cultures. To further enhance stability, e.g., in case of thin and/or large epidermal equivalents, as well as to increase adhesion of the silicone membrane, a thin layer of tissue glue, e.g. fibrin glue, may be applied before.

On-top coating (1) enhances stability and improves handling of the grafts, and (2) serves as a protective coat against physical damage as well as the proteolytic milieu and bacteria in the wound.

EXAMPLE 4

Shipping

On-top coated epidermal equivalents are detached from the culture insert membranes by incubation in diluted Dispase and then grasping the epidermal equivalents together with the silicone membrane using fine tweezers and transferring them on the membrane of an insert previously embedded in 0.7% agarose soaked with culture medium in the well of a multiwell dish. These dishes are then placed in the shipping container. For application to the wound bed, the epidermal equivalents are again grasped, together with the silicone membrane, which (1) serves for orientation of the graft (i.e., basal side down, cornified side up) and (2) by leaving it on the grafted epidermal equivalents in the wound serves as a protective coat (see above).

From the foregoing detailed description of the specific embodiments of the present invention, it should be readily apparent that a unique methodology for the selection and culture of keratinocytes from the outer root sheath (ORS) of hair follicles for subsequent use in, for example, skin grafting procedures, has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For example, the selection of anagen hairs are believed to be a matter of routine for a person of ordinary skill in the art with knowledge of the embodiments described herein.

We claim:

1. A method for the selection of keratinocyte precursor cells from the outer root sheath of hair for subsequent use in a composition for healing a skin defect, comprising the step of:

(a) plucking of an anagen or growing hair;

(b) primary-culturing the outer root sheath-derived keratinocyte precursor cells by adhering said anagen hair, in toto, to a microporous membrane, which possesses growth-arrested limited feeder cells on its undersurface so as to select for keratinocyte precursor cells from the outer root sheath of hair, wherein the primary culture medium contains human serum in a concentration less than 5%;

(c) organotypically-culturing the outer root sheath cells harvested from said primary cultures by modulating a microporous membrane which also possesses growth-arrested limited feeder cells on its undersurface, wherein the organotypic culture medium contains human serum in a concentration less than 5% and the keratinocyte precursor cells are seeded at a density of between $3\times10^4$ cells/cm$^2$ and $1\times10^5$ cells/cm$^2$;

(d) generating an epidermal or complex skin equivalent, for subsequent use as a graft insert, comprised of keratinocyte precursor cells by placing a carrier membrane on top of said organotypic-culture from step (c) and detaching said skin or epidermal equivalent, which is comprised of the keratinocyte precursor cells and carrier membrane, together as a single, laminat unit;

(e) contacting said epidermal or skin equivalent with a skin defect present on an individual, and immobilizing said epidermal or skin equivalent at the site of contact.

2. The method of claim 1, wherein said outer root sheath cells are autologous cells derived from the individual who will subsequently undergo treatment for a skin defect.

3. The method of claim 1, wherein said outer root sheath cells are homologous cells.

4. The method of claim 1, wherein the culture density of said growth-arrested limited feeder cells on said microporous membrane is between about $1\times10^4$ cells/cm$^2$ and about $5\times10^4$ cells cm$^2$.

5. The method of claim 1, wherein said growth-arrested limited feeder cells are banked or immobilized cells.

6. The method of claim 1, wherein said primary and organotypic cultures utilize autologous or homologous human serum.

7. The method of claim 1, wherein said epidermal or skin equivalent comprises outer root sheath cells cultured in a medium containing only homologous or autologous biological supplements.

8. The method of claim 1, wherein said epidermal or skin equivalent comprises outer root sheath cells cultured in a medium containing only homologous or autologous releasates from blood components.

9. The method of claims 1 or 8, wherein said epidermal or skin equivalent comprises outer root sheath cells cultured in a medium containing only homologous or autologous releasates from blood components at a concentration of about 0.1% to about 20%.

10. The method of claims 1 or 8, wherein said epidermal equivalents are coated on their top or cornified side with a fibrin glue.

11. The method of claims 1 or 10, wherein said epidermal equivalents are coated on their top or cornified side with a carrier membrane.

12. The method of claim 1, wherein said microporous membrane is coated by one or more extracellular matrix substances selected from a group consisting of: fibrin, fibronectin, collegens, laminins and hyaluronan.

13. The method of claims 1 or 12, wherein said microporous membrane possesses a growth-arrested limited feeder cell system on its undersurface with said feeder cells of at least one type of cell selected from the group comprising human dermal fibroblasts, epidermal cells, mesenchymal cells, neuronal cells and endothelial cells.

14. The method of claim 1, wherein said carrier membrane is made from one or more types of materials selected from the group comprising polyester, PTFE, polyurethane, hyaluronic acid, polylactic acid, collagen, or a silicone or vaseline gauze dressing.

15. The method of claim 1, wherein the size of said epidermal equivalent is selected from the group consisting of 1.0 cm, 1.5 cm, 2.0 cm, and 2.5 cm in diameter.

* * * * *